US009629846B1

(12) United States Patent
Greathouse et al.

(10) Patent No.: US 9,629,846 B1
(45) Date of Patent: Apr. 25, 2017

(54) NUTRITIONAL SUPPLEMENTS FOR WOMEN DESIRING TO BECOME PREGNANT, AND PREGNANT AND NURSING WOMEN

(71) Applicant: Argent Development Group, LLC, Mountain View, CA (US)

(72) Inventors: Kenneth R. Greathouse, Los Altos, CA (US); Rhett Sean Daniels, Santa Monica, CA (US)

(73) Assignee: Argent Development Group, LLC, Mountain View, CA (US)

(*) Notice: Subject to any disclaimer, the term of this patent is extended or adjusted under 35 U.S.C. 154(b) by 0 days.

(21) Appl. No.: 14/999,041

(22) Filed: Mar. 23, 2016

Related U.S. Application Data

(63) Continuation of application No. 14/121,769, filed on Oct. 16, 2014, now abandoned.

(60) Provisional application No. 61/962,692, filed on Nov. 14, 2013.

(51) Int. Cl.
| | | |
|---|---|---|
| *A01N 59/20* | (2006.01) |
| *A61K 31/519* | (2006.01) |
| *A61K 31/295* | (2006.01) |
| *A61K 31/202* | (2006.01) |
| *A61K 31/675* | (2006.01) |
| *A61K 31/7076* | (2006.01) |
| *A61K 31/661* | (2006.01) |
| *A61K 31/714* | (2006.01) |
| *A61K 33/34* | (2006.01) |
| *A61K 33/30* | (2006.01) |
| *A61K 31/191* | (2006.01) |
| *A61K 31/375* | (2006.01) |
| *A61K 9/48* | (2006.01) |
| *A61K 9/00* | (2006.01) |
| *A61K 31/315* | (2006.01) |
| *A61K 31/30* | (2006.01) |

(52) U.S. Cl.
CPC .......... *A61K 31/519* (2013.01); *A61K 9/0053* (2013.01); *A61K 9/4825* (2013.01); *A61K 31/191* (2013.01); *A61K 31/202* (2013.01); *A61K 31/295* (2013.01); *A61K 31/30* (2013.01); *A61K 31/315* (2013.01); *A61K 31/375* (2013.01); *A61K 31/661* (2013.01); *A61K 31/675* (2013.01); *A61K 31/7076* (2013.01); *A61K 31/714* (2013.01); *A61K 33/30* (2013.01); *A61K 33/34* (2013.01)

(58) Field of Classification Search
USPC ....................................................... 424/638
See application file for complete search history.

(56) References Cited

U.S. PATENT DOCUMENTS

| | | |
|---|---|---|
| 4,725,427 A | 2/1988 | Ashmead et al. |
| 5,292,538 A | 3/1994 | Paul et al. |
| 5,516,925 A | 5/1996 | Pedersen et al. |
| 5,795,873 A | 8/1998 | Allen |
| 5,817,659 A | 10/1998 | Muller et al. |
| 5,869,084 A | 2/1999 | Paradissis et al. |
| 5,932,624 A | 8/1999 | Herbert |
| 5,997,915 A | 12/1999 | Bailey et al. |
| 6,160,116 A | 12/2000 | Muller et al. |
| 6,254,904 B1 | 7/2001 | Bailey |
| 6,271,374 B1 | 8/2001 | Muller et al. |
| 6,299,896 B1 | 10/2001 | Cooper et al. |
| 6,361,800 B1 | 3/2002 | Cooper et al. |
| 6,368,621 B1 | 4/2002 | Engel et al. |
| 6,441,168 B1 | 8/2002 | Muller et al. |
| 6,458,981 B1 | 10/2002 | Ashmead et al. |
| 6,488,956 B1 | 12/2002 | Paradissis et al. |
| 6,521,247 B1 | 2/2003 | de Vries |
| 6,528,496 B1 | 3/2003 | Allen et al. |
| 6,673,381 B2 | 1/2004 | Bailey et al. |
| 6,716,814 B2 | 4/2004 | Ericson et al. |
| 6,808,725 B2 | 10/2004 | Bailey et al. |
| 6,953,588 B2 | 10/2005 | Cooper et al. |
| 7,172,778 B2 | 2/2007 | Bailey et al. |
| 7,674,490 B2 | 3/2010 | Bailey et al. |
| 7,704,542 B2 | 4/2010 | Bydlon et al. |
| 7,964,189 B1 | 6/2011 | Morrison et al. |
| 7,981,858 B1 | 7/2011 | Lang |
| 7,994,217 B2 | 8/2011 | Nidamarty et al. |
| 8,007,846 B2 | 8/2011 | Thompson et al. |
| 8,007,853 B2 | 8/2011 | Bydlon et al. |
| 8,075,910 B2 | 12/2011 | Schramm et al. |
| 8,168,611 B1 | 5/2012 | Perrin et al. |
| 8,173,160 B2 | 5/2012 | Schramm et al. |
| 8,178,709 B2 | 5/2012 | Nelson et al. |
| 8,183,227 B1 | 5/2012 | Perrin et al. |
| 8,425,956 B2 | 4/2013 | Thompson et al. |
| 8,454,950 B2 | 6/2013 | Haschke et al. |
| 8,454,951 B2 | 6/2013 | Morrison et al. |
| 8,470,352 B2 | 6/2013 | Liu et al. |
| 8,491,937 B2 | 7/2013 | Goldberg et al. |
| 8,535,659 B1 | 9/2013 | Morrison et al. |
| 8,535,660 B1 | 9/2013 | Morrison et al. |
| 8,637,061 B2 | 1/2014 | Liu et al. |
| 2006/0134227 A1 | 6/2006 | Bortz et al. |
| 2007/0270591 A1 | 11/2007 | Ashmead |
| 2009/0124572 A1 | 5/2009 | Nelson |
| 2012/0100123 A1 | 4/2012 | Gongzalez et al. |

*Primary Examiner* — Devang Thakor
(74) *Attorney, Agent, or Firm* — Joseph I. Hirsch

(57) ABSTRACT

The present invention relates to nutritional supplements to be administered to, or to be taken by, women desiring to become pregnant, and pregnant and nursing women. The nutritional supplements of this invention have a unique blend of one or more folic acid materials, vitamins and minerals and a nutritionally acceptable carrier therefor. The invention describes specific nutritional supplements for the uses set forth above.

11 Claims, No Drawings

NUTRITIONAL SUPPLEMENTS FOR WOMEN DESIRING TO BECOME PREGNANT, AND PREGNANT AND NURSING WOMEN

CROSS-REFERENCE TO RELATED APPLICATION

This application is based upon, and claims priority from, U.S. provisional application Ser. No. 61/962,692, filed Nov. 14, 2013, the disclosure of which is incorporated herein by this reference. This application is a continuation of application Ser. No. 14/121,769, filed Oct. 16, 2014.

FIELD OF THE INVENTION

The present invention relates to nutritional supplements to be administered to, or to be taken by, women desiring to become pregnant, and pregnant and nursing women.

BACKGROUND OF THE INVENTION

The present invention relates to nutritional supplements to be administered to, or to be taken by, women desiring to become pregnant, and pregnant and nursing women. Increased incidence of birth defects (e.g., neural tube defects) has been linked to mothers with various nutritional deficiencies. It is known that there are numerous deficiencies in the diets of pregnant and nursing women, particularly, but not exclusively, women of low and moderate incomes. More broadly, diets of people in general, and women in particular, in the United States are known to be poor, due in part to the prevalence of so-called "junk food", fast food, which is high in caloric content, but low in nutritional value, and the desire of many working people to eat prepared food after a long day at the office. One example of this is witnessed in the high-omega-6/omega-3 fatty acid ratio (some studies have documented ratios of nearly 17 to 1) seen in the Western diet. In addition, many commonly prescribed medications cause nutrient depletion. The widely used anti-diabetic drug metformin, for instance, has been shown to reduce folate, magnesium, and Vitamin $B_{12}$ levels. Furthermore, individuals may possess genetic polymorphisms that diminish their ability to metabolize dietary nutrients. For example, patients with defective intestinal conjugase activity may not be able to effectively metabolize natural folates, which exist in the polyglutamate form. For women of child-bearing age, the situation becomes worse when they become pregnant and thereafter during pregnancy as what the fetus needs may not be provided by a given woman's normal daily dietary intake. Another obstacle to achieving a healthful, proper pregnancy diet is the nausea experienced during the early part of pregnancy.

Many supplements have been proposed and are currently being marketed in the United States to overcome the nutritional deficiencies caused by such eating habits. For example, Hermelin et al. in U.S. Pat. Nos. 6,258,466, 6,576,666 and 7,112,609 describe in the Background of the Invention sections of their respective inventions, various formulations and supplements, including prenatal formulations and supplements, that are (or were) on the market in the United States and contain various combinations of ingredients to supplement the nutrition, among others, of pregnant and nursing women. Such products are known by the names Materna, Enfamil, Natalins RX, Prenate Ultra, Niferex-PN, Niferex-PN Forte, Advanced Formula Zenate, Precare, and Natafort, all marketed by various companies that own the trademarked names of these products. See also Meyrowitz U.S. Pat. No. 7,238,373, Giordano et al. U.S. Pat. Nos. 7,390,509 and 7,560,123, Lane U.S. Pat. No. 7,572,462, Morrison et al. U.S. Pat. No. 7,964,189 and U.S. Pat. No. 8,454,951, and Nidamarty et al. U.S. Pat. No. 7,994,217.

Many of the supplements described above, and elsewhere in the literature, including those supplements currently on the market in the United States, contain a broad range of ingredients, many of which are not necessary to be administered to pregnant or nursing women. Some of these ingredients, while generally safe, may not be optimal choices for certain populations. Heme iron, for example while highly bioavailable, is not always the best option for prenatal iron supplementation. However, commonly used forms of non-heme iron cause gastrointestinal distress, which undermines individual or patient compliance. While ingredients used in currently available supplements may not do any harm, in the sense that the body will eliminate in one way or another that which is not needed, there is a preference, and it is our desire, to set forth unique supplement formulations that have those, and only those, ingredients that serve necessary and beneficial purposes, particularly for pregnant and nursing women, or women desiring to become pregnant.

BRIEF SUMMARY OF THE INVENTION

The unique nutritional supplements of the present invention are particularly suited for being administered to, or to be taken by, pregnant and nursing women and are free or substantially free (as those words are defined below) of any other added vitamins and minerals. However, they may also be administered to, or taken by, women desiring to become pregnant, so that any ensuing pregnancy (and thus the fetus) will be nutritionally supplemented from the very beginning of gestation.

The unique nutritional supplements of the present invention are exemplified by the following specific embodiments.

The nutritional supplements of the present invention consist essentially of a daily dose of nutritionally effective amounts of:

one or more materials selected from the group consisting of folic acid, a citrated folic acid material, folinic acid, the methylfolate derivatives thereof, and the nutritionally acceptable salts thereof,
  iron,
  docosahexaenoic acid,
  Vitamin $B_1$,
  Vitamin $B_2$,
  Vitamin $B_3$,
  Vitamin $B_6$,
  Vitamin $B_{12}$,
  Vitamin C,
  optionally copper and zinc together,
  optionally magnesium, and
  a nutritionally acceptable carrier therefor.

In a presently preferred embodiment of the present invention, nutritional supplements consist essentially of a daily dose of:
  about 0.1 mg to about 5 mg of one or more folic acid materials selected from the group consisting of folic acid, folinic acid, the methylfolate derivatives thereof, the nutritionally acceptable salts thereof, and an amount of a citrated folic acid material containing about 0.1 mg to about 5 mg of folic acid, preferably at least about 1 mg of folic acid,
  about 10 mg to about 120 mg of elemental iron,
  about 50 mg to about 600 mg of docosahexaenoic acid,
  about 10 mcg to about 1,500 mcg of Vitamin $B_1$, about 10 mcg to about 1,500 mcg of Vitamin $B_2$,
about 10 mcg to about 1,500 mcg of Vitamin $B_3$,
about 0.5 mg to about 50 mg of Vitamin $B_6$,
about 10 mcg to about 5,000 mcg of Vitamin $B_{12}$,
about 10 mg to about 70 mg of Vitamin C,
optionally about 1 mg to about 3 mg of elemental copper and about 1 mg to about 30 mg of elemental zinc together,
optionally 0.1 mg to about 100 mg of magnesium, and a nutritionally acceptable carrier therefor.

In another presently preferred embodiment of the present invention, a nutritional supplement consists essentially of a daily dose of:

about 1 mg to about 2.5 mg of one or more materials selected from the group consisting of folic acid, folinic acid, the methylfolate derivatives thereof, and the nutritionally acceptable salts thereof, and an amount of a citrated folic acid material containing about 1 mg to about 2.5 mg of folic acid, preferably at least about 1 mg of folic acid,
about 20 mg to about 35 mg of elemental iron,
about 100 mg to about 300 mg of docosahexaenoic acid,
about 20 mcg to about 625 mcg of Vitamin $B_1$,
about 20 mcg to about 625 mcg of Vitamin $B_2$,
about 20 mcg to about 625 mcg of Vitamin $B_3$,
about 0.5 mg to about 5 mg of Vitamin $B_6$,
about 100 mcg to about 600 mcg of Vitamin $B_{12}$,
about 10 mg to about 70 mg of Vitamin C,
optionally about 1 mg to about 3 mg of elemental copper and about 5 mg to about 15 mg of elemental zinc together, and
optionally about 2.5 mg to about 7.5 mg of magnesium, and
a nutritionally acceptable carrier therefor.

In an exemplary embodiment of the present invention, the nutritional supplements include a daily dose of:

about 1 mg to about 2.5 mg of one or more of the group consisting of folic acid, folinic acid, 6S)-tetrahydrofolic acid, 5-methyl-(6S)-tetrahydrofolic acid, 5-formyl-(6S)-tetrahydrofolic acid, 5-formyl-(6S)-tetrahydrofolic acid, 10-formyl-(6R)-tetrahydrofolic acid, 5,10-methylene-(6R)-tetrahydrofolic acid, 5,10-methenyl-(6R)-tetrahydrofolic acid, and 5-formimino-(6S)-tetrahydrofolic acid and the nutritionally acceptable salts thereof, and an amount of a citrated folic acid material containing about 1 mg to about 5 mg of folic acid, preferably at least about 1 mg of folic acid,
about 25 mg to about 30 mg of elemental iron administered in the form of a nutritionally acceptable iron amino acid chelate,
about 100 mg to about 250 mg of docosahexaenoic acid, in addition to the vitamins and mineral(s) set forth above and a nutritionally acceptable carrier therefor.

In exemplary embodiments of the present invention, nutritional supplements of the present invention consist of a daily dose of:

about 1 mg of folic acid or an amount of a citrated folic acid material containing about 1 mg of folic acid,
about 27 mg of elemental iron administered in the form of an iron amino acid chelate prepared according to the process described in U.S. Pat. No. 7,341,708 using aspartic acid and cysteine,
about 200 mg of docosahexaenoic acid derived from fish oil having greater than 75% docosahexaenoic acid and less than 5% eicosapentaenoic acid,
about 25 mcg, 125 mcg or 625 mcg of Vitamin $B_1$ administered as thiamine pyrophosphate,
about 25 mcg, 125 mcg or 625 mcg of Vitamin $B_2$ administered as flavin adenine dinucleotide hydrate,
about 25 mcg, 125 mcg or 625 mcg of Vitamin $B_3$ administered as nicotinamide adenine dinucleotide hydrate,
about 1 mg of Vitamin $B_6$ administered as pyridoxal 5' phosphate,
about 500 mcg of Vitamin $B_{12}$ administered as about 250 mcg of 5'-deoxyadensosyl-cobalamin and about 250 mcg of methylcobalamin,
about 15 mg of Vitamin C administered as a mixture of magnesium ascorbate and zinc ascorbate (the magnesium and zinc in this exemplary supplement being provided via the magnesium ascorbate and zinc ascorbate, respectively), and
a nutritionally acceptable carrier therefor.

In other exemplary embodiments of the present invention, nutritional supplements of the present invention consist of a daily dose of:

about 1 mg of folic acid or an amount of a citrated folic acid material containing about 1 mg of folic acid,
about 30 mg of elemental iron administered in the form of an iron amino acid chelate prepared according to the process described in U.S. Pat. No. 7,341,708 using aspartic acid and cysteine,
about 200 mg of docosahexaenoic acid derived from fish oil having greater than 75% docosahexaenoic acid and less than 2% eicosapentaenoic acid,
about 25 mcg, 125 mcg or 625 mcg of Vitamin $B_1$ administered as thiamine pyrophosphate,
about 25 mcg, 125 mcg or 625 mcg of Vitamin $B_2$ administered as flavin adenine dinucleotide hydrate,
about 25 mcg, 125 mcg or 625 mcg of Vitamin $B_3$ administered as nicotinamide adenine dinucleotide hydrate,
about 1 mg of Vitamin $B_6$ administered as pyridoxal 5' phosphate,
about 500 mcg of Vitamin $B_{12}$ administered as about 250 mcg of 5'-deoxyadensosyl-cobalamin and about 250 mcg of methylcobalamin,
about 50 mg of Vitamin C administered as sodium ascorbate,
about 5 mg of elemental magnesium administered as magnesium 1-threonate, and
a nutritionally acceptable carrier therefor.

In yet other exemplary embodiments of the present invention, nutritional supplements of the present invention consist of a daily dose of:

about 1 mg of folic acid or an amount of a citrated folic acid material containing about 1 mg of folic acid,
about 30 mg of elemental iron administered in the form of an iron amino acid chelate prepared according to the process of U.S. Pat. No. 7,341,708 using aspartic acid and cysteine,
about 200 mg of docosahexaenoic acid derived from fish oil having greater than 75% docosahexaenoic acid and less than 1% eicosapentaenoic acid,
about 25 mcg, 125 mcg or 625 mcg of Vitamin $B_1$ administered as thiamine pyrophosphate,
about 25 mcg, 125 mcg or 625 mcg of Vitamin $B_2$ administered as flavin adenine dinucleotide hydrate,
about 25 mcg, 125 mcg or 625 mcg of Vitamin $B_3$ administered as nicotinamide adenine dinucleotide,
about 1 mg of Vitamin $B_6$ administered as pyridoxal 5' phosphate,
about 500 mcg of Vitamin $B_{12}$ administered as about 250 mcg of 5'-deoxyadensosyl-cobalamin and about 250 mcg of methylcobalamin,
about 50 mg of Vitamin C administered as sodium ascorbate,
about 5 mg of elemental magnesium administered as magnesium 1-threonate, and
a nutritionally acceptable carrier therefor.

The preferred form of administration of the nutritional supplements of the present invention are soft gelatin capsules, taken once or twice daily in the daily amounts set forth above, for example, in the morning along with breakfast or after any early morning nausea has passed. The ingredients may be administered in two or more soft gelatin capsules where the various ingredients of the unique nutritional supplements of the present invention are separated into different soft gelatin capsules, which are taken (preferably) at the same time. The capsules may be either liquid-filled or powder-filled, although the presently preferred dosage form is oil-based liquid-filled capsules.

DETAILED DESCRIPTION OF THE INVENTION

Folic acid is probably the most important vitamin during pregnancy. The requirement increases significantly in pregnancy and a deficiency of this vitamin is prevalent among American women. The cardinal result of folic acid deficiency is a maternal anemia that is significantly increased during pregnancy. It has been estimated that 2.5% to 5% of pregnant women in the United States are folic acid-deficient and this is particularly true in indigent patients, adolescents, or those having successive pregnancies with short intervals between them. A deficiency of folic acid results in fetal neural tube defects, preterm delivery, placental abruption and growth restricted fetuses. Since foods in this country are not fortified with folic acid, the nutritional supplements of the present invention include about 0.1 mg/day to about 5 mg/day, preferably about 1 mg/day to about 2.5 mg/day, for example about 1 mg/day, about 1.2 mg/day or about 2 mg/day, of one or more of the group consisting of folic acid (as pteroylglutamic acid), folinic acid (as formyltetrahydrofolate), and methylfolate (as methyltetrahyrdrofolate), such as, for example, ((6S)-tetrahydrofolic acid, 5-methyl-(6S)-tetrahydrofolic acid, 5-formyl-(6S)-tetrahydrofolic acid, 5-formyl-(6S)-tetrahydrofolic acid, 10-formyl-(6R)-tetrahydrofolic acid, 5,10-methylene-(6R)-tetrahydrofolic acid, 5,10-methenyl-(6R)-tetrahydrofolic acid, and 5-formimino-(6S)-tetrahydrofolic acid, and the nutritionally acceptable salts thereof. Exemplary folic acid materials are about 1 mg of folic acid, about 1.2 mg of the calcium salt of 1-methylfolate [6(S)-5-methyltetrahydrofolate)]; a mixture of 1 mg of a citrated folic acid material (controlled release) and 1 mg of the levomefolic acid moiety from 6(S)-5-methyltetrahydrofolic acid; a mixture of about 0.4 mg of a citrated folic acid material (controlled release) and about 0.8 mg of levofolinic acid moiety as the sodium salt of 6(S)-5-formyl-tetrahydrofolic acid; and an amount of a citrated folic acid material containing about 1 mg of folic acid. Citrated folic acid can be prepared according to the methods described in co-pending application Ser. No. 14/053,926, filed Oct. 15, 2013, in the name of Rhett Sean Daniels. The folic acid and the citrate buffer(s) need to be bound together with an appropriate binder for formulation into the nutritional supplements of the present invention. That citrated folic acid material may contain, for example, about 5% folk acid active, so in this example about 20 mg of the citrated folic acid material would contain about 1 mg of folic acid. Other percentages of folic acid in the citrated folic acid material are possible.

Because of the blood formation requirements of the fetus and placenta, iron depletion and iron deficiency anemia make this the most common deficiency in pregnancy (90% of all anemias). Heme iron, which is derived from hemoglobin and myoglobin found in meats, is much better absorbed than non-heme, which is found mostly in foods of plant origin (30% versus 5% absorption). Women who are vegetarians absorb much less iron than needed during pregnancy. Growth restriction, preterm delivery, and pre-eclampsia have been noted in women who have iron deficiency anemia. One of the problems with iron supplementation is upper GI irritation resulting in nausea, vomiting and a decreased appetite as well as constipation. Thus, to mitigate both of these problems, the nutritional supplements of the present invention include about 10 mg/day to about 120 mg/day, for example about 20 mg/day to about 35 mg/day, or about 27 mg/day or 30 mg/day of elemental iron preferably administered as an iron amino acid chelate. A presently preferred form of the iron material is an iron amino acid chelate, such as AminoFerr™, a form of iron containing pure chelated material without interfering ions, thus resulting in high solubility and adsorption. AminoFerr is a product of Viva Pharmaceuticals, Inc. of Richmond, British Columbia, Canada and is prepared according to the process of U.S. Pat. No. 7,341,708 (which is incorporated herein by this reference) using aspartic acid and cysteine. The AminoFerr has ferrous gluconate as a base or carrier during production, but the final product is without iron salt (that is, it is in pure iron amino acid chelate form) and is used as such in the nutritional supplements of the present invention. The amount of the iron-containing compound used will be the amount that will give, for example about 25 mg/day to about 30 mg/day, or about 27 mg/day, of elemental iron content. Other amino acids, such as those described in U.S. Pat. No. 7,341,708, for example at the top of column 4 thereof, can be used in the preparation of other iron amino acid chelates suitable for use in the nutritional supplements of the present invention.

Omega-3 fatty acids found in marine fats have been shown to be important in the prevention of pre-eclampsia, preterm delivery and premature rupture of the membranes. Enhanced, cognitive function and improved visual acuity in babies born to mothers supplemented with docosahexaenoic acid have also been noted. Finally, there has been a decrease in maternal postpartum depression when supplemented with docosahexaenoic acid. Cold water fish are the highest dietary sources of docosahexaenoic acid and it is also available in the eggs of chickens supplemented with microalgae. Unfortunately, supplementation from these two sources is rare in this country and, therefore, the nutritional supplements of the present invention include about 50 mg/day to about 600 mg/day, for example about 100 mg/day to about 300 mg/day, for example 200 mg/day, of docosahexaenoic acid, which is a beneficial amount for pregnant women. A suitable source of docosahexaenoic acid is fish oil, for example tuna oil (or tuna/anchovy oil), from AK BioTech Co., Inc., Nam-gu. Ulsan, South Korea, which has >75% docosahexaenoic acid and <5% eicosapentaenoic acid, preferably <2% eicosapentaenoic acid and, most preferably <1% eicosapentaenoic acid. Another company that is a source of suitable docosahexaenoic acid in fish oil for use in the present invention is Chemport Inc., Naju-si, Jeollanam-do, South Korea.

Vitamin $B_1$ is very important in red blood cell formation and all of the ingredients of fetal blood cells. Deficiency in the mother can result in acute fetal cardiac failure from significant anemia in the fetus. Since this vitamin is not ubiquitous in a normal diet, the nutritional supplements of the present invention include about 10 mcg/day to about 1,500 mcg/day of Vitamin $B_1$, for example about 20 mcg/day to about 625 mcg/day, or about 25 mcg/per day, about 125 mcg/day or about 625 mcg/day as thiamine (e.g., thiamine pyrophosphate), to enhance red blood cell formation.

The requirements for Vitamin $B_2$ increase during pregnancy. Deficiency has been associated with fetal malformation of the bony tissue and membranous skeleton, which precedes the cartilageous and osseous skeletons. A deficiency of Vitamin $B_2$ is also linked to hyperemesis gravidarum and an increased incidence of growth restriction and preterm delivery in the fetus. Maternal deficiency of Vitamin $B_2$ is associated with stomatitis, glossitis and cheilosis. The nutritional supplements of the present invention include about 10 mcg/day to about 1,500 mcg/day, for example about 20 mcg/day to about 625 mcg/day, or about 25 mcg/day, about 125 mcg/day or about 625 mcg/day of Vitamin $B_2$, as flavin adenine dinucleotide hydrate, to mitigate any deficiency of this vital material during pregnancy.

Vitamin $B_3$ is necessary for appropriate fetal growth and for the proper functioning of cellular enzyme systems. In animals, small for gestational age offsprings are much more common when there is a deficiency of Vitamin $B_3$. Vitamin $B_3$ is also important for transforming carbohydrates into energy. The nutritional supplements of the present invention include about 10 mcg/day to about 1,500 mcg/day, for example about 20 mcg/day to about 625 mcg/day, or about 25 mcg/day, about 125 mcg/day or about 625 mcg/day, of Vitamin $B_3$ as nicotinamide adenine dinucleotide.

Vitamin $B_6$ (pyridoxine) is used by obstetricians to combat hyperemesis of pregnancy. During pregnancy $B_6$ levels in the plasma fall to as low as 25% of non-pregnant levels. This suggests there is an increased utilization of pyridoxine during gestation. Vitamin $B_6$ and folic acid have been shown to be associated with the lower risk of coronary artery disease particularly among women. While Vitamin $B_6$ is present in meat, whole grain breads and cereals as well as vegetables, it is particularly diminished among patients at high risk for inadequate nutrition (substance abuse, adolescents, short intervals between pregnancies, multi-fetal pregnancies, and women on restricted intake such as vegan diets). Among animals, Vitamin $B_6$ deficiency during pregnancy is associated with severe growth retardation, hypoplasia of the thymus and neonatal death as well as reduced immunologic competence. While there is no direct evidence of adverse effects of such deficiency in humans, volunteer studies among non-pregnant adults have shown that Vitamin $B_6$ deficiency can cause skin manifestations and some central nervous system defects. Further low levels tend to persist after pregnancy and during lactation and are also lower in cord blood and in the milk of such women. Accordingly, the nutritional supplements of the present invention include about 0.5 mg/day to about 50 mg/day, for example about 1 mg/day, as pyridoxal 5' phosphate.

Vitamin $B_{12}$ is essential for appropriate folic acid metabolism, a deficiency of which is noted by megaloblastic anemia. It also plays a role in maintaining cellular integrity of the central nervous system. Therefore, while supplementation of folic acid may cure hematologic symptoms (anemia) of $B_{12}$ deficiency, it will leave the fetus vulnerable to central nervous system damage. Vitamin $B_{12}$ is found exclusively in animal tissues hence during pregnancy a vegan woman is at risk for $B_{12}$ deficiency. Accordingly, the nutritional supplements of the present invention include about 10 mcg/day to about 1,000 mcg/day of Vitamin $B_{12}$, preferably about 100 mcg/day to about 600 mcg/day, for example about 500 mcg/day, for example in equal parts of 5'-deoxyadenosylcobalamin (about 250 mcg) and methylcobalamin (about 250 mcg), to mitigate any deficiency of this essential vitamin.

Vitamin C (ascorbic acid) is essential for the formation of collagen and therefore is very important for both mother and fetus during pregnancy. The transport mechanism across the placenta is the same for that of glucose therefore Vitamin C supplementation is very important in those women having (or at risk for) diabetes. There is a progressive drop in Vitamin C levels during each trimester and if serum levels of this ingredient drop below 80 mg/day habitual abortion, preterm birth and premature rupture of the membranes may occur. Since there are vagaries of absorption during pregnancy, the nutritional supplements of the present invention include about 10 mg/day to about 70 mg/day, for example about 50 mg/day, of Vitamin C supplementation in the form of ascorbic acid or one or more nutritionally acceptably salts thereof (for example, sodium ascorbate, magnesium ascorbate and/or zinc ascorbate). For example, about 56 mg of sodium ascorbate contains about 50 mg of Vitamin C.

Of all the trace elements, copper has received attention as probably being the most important in human gestation. The metabolism of this element is more altered by pregnancy than any other state. While serum copper rises during pregnancy, due to hormonal changes and protein binding efficiency, levels of copper are low in the fetus; therefore, it is important to supplement this trace element in the diet of pregnant women. Copper is also important as it is associated with a protein in the fetal mitochondria, which disappears shortly after birth. This mitochondrial function is important in most oxidative reactions in rapidly developing fetal tissues. Accordingly, the nutritional supplements of the present invention optionally include about 1 mg/day to about 3 mg/day, preferably about 2 mg/day, of elemental copper to ensure that pregnant and nursing women have appropriate levels of copper during these important stages. However, if copper is optionally added, zinc as described below should also be added in the same nutritional supplement. Although any nutritionally acceptable source of copper will suffice, and many are generally known, a suitable copper material is a copper amino acid chelate that is a product of Viva Pharmaceuticals, Inc. of Richmond, British Columbia, Canada, which is prepared according to the process of U.S. Pat. No. 7,341,708 using aspartic acid and lysinc. Other amino acids, such as those described in U.S. Pat. No. 7,341,708, for example at the top of column 4 thereof, can be used in the preparation of other copper amino acid chelates suitable for use in the present invention.

Zinc deficiency produces congenital malformations as well as fetal losses. Since maternal plasma levels of zinc decrease during pregnancy, supplementation is important. In the fetus deficiency of zinc may be involved with premature rupture of the membranes and a reduced ability to fight infection due to suppressed immunity. Zinc deficiency is quite common in the United States, particularly in pregnant women and, therefore, the nutritional supplements of the present invention optionally include about 1 mg/day to about 30 mg/day, for example about 5 mg/day to about 15 mg/day or about 10 mg/day, of elemental zinc. However, if zinc is optionally added, copper as described above should also be added in the same nutritional supplement. Although any nutritionally acceptable source of zinc will suffice, and many are generally known, a suitable zinc material is a zinc amino acid chelate of Viva Pharmaceuticals, Inc. of Richmond, British Columbia, Canada, which is prepared according to the process of U.S. Pat. No. 7,341,708 using aspartic acid and lysine. Other amino acids, such as those described in U.S. Pat. No. 7,341,708, for example at the top of column 4 thereof, can be used in the preparation of other zinc amino acid chelates suitable for use in the present invention.

Magnesium deficiency has been linked to pre-eclampsia, premature rupture of the membranes and preterm births secondary to early labor. Women who deliver prematurely are more likely to have lower plasma levels of this mineral. The nutritional supplements of the present invention optionally include about 0.1 mg/day to about 100 mg/day, for example about 2.5 mg/day to about 7.5 mg/day, or about 5 mg/day, of elemental magnesium, for example administered as about 60 mg of magnesium l-threonate that contains about 5 mg of elemental magnesium, to supplement any deficiencies that may occur.

Vitamin $B_1$, Vitamin $B_2$, Vitamin $B_3$ and Vitamin $B_{12}$ can be administered in mcg amounts, as shown above, if administered in "body ready" form, thus bypassing genetic defects that prevent vitamin absorption that is common in all people. The most reduced forms of vitamins decrease the likelihood that there would be inhibition of vitamin metabolism, and increase the likelihood that vitamin supplementation may be achieved in the face of genetic defects (sometimes referred to as genetic polymorphisms). Furthermore, by supplying minimally acceptable amounts of reduced forms of vitamins the chance of overdosing is decreased and the action of folate-iron nutritional supplements for the therapeutic indication (e.g., iron supplementation or prenatal supplementation) is not adversely affected.

All of the ingredients of the present invention (with the exception of the citrated folic acid material) are well known and are commercially available, generally from multiple sources. The iron amino acid chelate (e.g., AminoFerr), the copper amino acid chelate and the zinc amino acid chelate may be obtained from Viva Pharmaceuticals, Inc. of Richmond, British Columbia, Canada. The ingredients may be used in any chemical form known that are suitable for use in nutritional supplements, except that, in certain instances as set forth above, particularly with regard to the preferred and particularly preferred embodiments of the present invention, specific forms are desired. In addition, the methods of manufacture thereof are well known to those skilled in this art (or described in the above identified co-pending application) and need not be described further herein.

The nutritional supplements of the present invention include any suitable nutritionally acceptable carrier as would be known to one skilled in this art. The methods of nutritional formulation applicable to the supplements of the present invention are also well known to one skilled in this art and need not be described further herein. Suitable carriers and methods of formulation are shown, for example, in Remington's Pharmaceutical Sciences (and other publications in the field of pharmaceutical or nutrition formulation) and in the Hermelin et al. and other patents cited above and, to the extent necessary, the disclosures thereof pertaining thereto are incorporated herein by this reference. Suitable carrier materials include, for example, citric acid, bovine gelatin, glycerin, glycine, hesperidin complex (a citrus bioflavinoid), 1-lysine acetate, 1-glutathione, lecithin, olive oil, purified water, tripotassium citrate, and yellow beeswax and various flavorings, such as caramel and orange flavorings. Any dosage form as appropriate may be utilized, although, given the nature of the ingredients described herein, soft gelatin capsules, using conventional nutritionally acceptable ingredients, are satisfactory and is the preferred form of administration, although other dosage forms may be used as well. A single daily capsule taken orally will suffice, generally to be taken at breakfast so as not to be forgotten during the day, although if desired, smaller (e.g., two) capsules can be utilized, for example, ones where the folic acid materials, the iron and the docosahexaenoic acid are in one capsule and the other ingredients are in a second capsule. The docosahexaenoic acid can also be in its own dosage form (generally a separate capsule), which can be taken at the same time as the other ingredients or at a different time if so desired. The capsules may be either liquid-filled or powder-filled, although the presently preferred dosage form is oil-based liquid-filled capsules. These nutritional supplements are particularly suited for being administered to, or to be taken by, pregnant and nursing women and are free or substantially free (as those words are defined below) of any other added vitamins and minerals. However, they may also be administered to, or to be taken by, women desiring to become pregnant, so that any ensuing pregnancy (and thus the fetus) will be nutritionally supplemented from the very beginning of gestation.

The embodiments of the present invention can be or are, as shown below in the Examples, free or substantially free of other added vitamins and minerals. For example, the nutritional supplements of the present invention do not include Vitamin $B_5$ or Vitamin $B_7$; and do not include calcium or other essential (e.g., omega-3 or omega-6) fatty acids in other than trace or carrier quantities as might be present in certain carrier materials. Thus, the phrases "consisting essentially of" and "consisting of" should be construed as set forth in MPEP 2111.03 (Transitional Phrases). Thus, the above phrases and the phrase "free or substantially free of any other added vitamins and minerals" should be construed as precluding the presence of additional ingredients in nutritionally effective amounts (particularly those that are intentionally added in nutritionally effective amounts), but not preclude them in trace amounts or quantities that are present (or inherently present as in the case of the docosahexaenoic acid fish oil) in other than nutritionally effective amounts, for example as part of the recited nutritionally acceptable carrier or as a minor impurity resulting from the production or manufacture of a recited material, such as the docosahexaenoic acid. Such a carrier will generally be, as is well known in this field, a multi-component carrier having many ingredients and the diluents, binders and adhesives, lubricants, plasticizers, disintegrants, colorants, bulking substances, flavorings, sweeteners, buffers, adsorbents, etc. referred to, for example, by Hermelin et al. U.S. Pat. No. 6,576,666 (column 14, lines 39 et seq.) cited above that may include, as is known in this art, some vitamins, minerals or essential fatty acids in trace or carrier (but not nutritionally effective) quantities. The presence of such ingredients in trace or carrier quantities, for example in such a multi-component carrier or as a trace or minor impurity in a recited ingredient, is considered by Applicants to still be within the scope of claims having "consisting essentially of", "consisting of" and/or "free or substantially free of any other added vitamins and minerals" language, as long as nutritionally effective amounts or quantities of such ingredients are not intentionally added or used. The enumerated ingredients of the present invention would generally be listed as the "active" ingredients on the product label, while other ingredients, particularly those present in less than nutritionally effective amounts, such as, for example, carrier materials, are generally listed as "inactive" ingredients.

The following embodiments of the present invention as set forth in the Examples are each prepared as either one or two soft gelatin capsules having the ingredients as shown (on a label claim basis) to be taken daily to supplement the nutritional diet of a woman desiring to become pregnant, or a pregnant or nursing woman.

EXAMPLES

Example 1

A nutritional supplement having a daily dose of:
about 1.2 mg of the calcium salt of 1-methylfolic acid [6(S)-5-methyltetrahydrofolic acid],
about 27 mg of elemental iron administered in the form of about 245 mg of an iron amino acid chelate prepared using aspartic acid and cysteine according to the process of U.S. Pat. No. 7,341,708,
about 200 mg of docosahexaenoic acid derived from fish oil having greater than 75% docosahexaenoic acid and less than 1% eicosapentaenoic acid,
about 25 mcg of Vitamin $B_1$ administered as thiamine pyrophosphate,
about 25 mcg of Vitamin $B_2$ administered as flavin adenine dinucleotide hydrate,
about 25 mcg of Vitamin $B_3$ administered as nicotinamide adenine dinucleotide,
about 1 mg of Vitamin $B_6$ administered as pyridoxal 5' phosphate,
about 500 mcg of Vitamin $B_{12}$ administered as about 250 mg of 5'-deoxyadensosyl-cobalamin and about 250 mcg of methylcobalamin,
about 15 mg of Vitamin C administered as equal amounts of magnesium ascorbate and zinc ascorbate (the magnesium and zinc in this exemplary supplement being provided via the magnesium ascorbate and zinc ascorbate, respectively), and
a nutritionally acceptable carrier therefor.

Example 2

A nutritional supplement having a daily dose of:
about 1 mg of the calcium salt of 1-methylfolic [6(S)-5-methyltetrahydrofolic acid] and about 1 mg of citrated folic acid (controlled release),
about 30 mg of elemental iron administered in the form of about 272 mg of an iron amino acid chelate prepared according to the process of U.S. Pat. No. 7,341,708 using aspartic acid and cysteine,
about 200 mg of docosahexaenoic acid derived from fish oil having greater than 75% docosahexaenoic acid and less than 1.5% eicosapentaenoic acid,
about 25 mcg of Vitamin $B_1$ administered as thiamine pyrophosphate,
about 25 mcg of Vitamin $B_2$ administered as flavin adenine dinucleotide hydrate,
about 25 mcg of Vitamin $B_3$ administered as nicotinamide adenine dinucleotide,
about 1 mg of Vitamin $B_6$ administered as pyridoxal 5' phosphate,
about 500 mcg of Vitamin $B_{12}$ administered as about 250 mcg of 5'-deoxyadensosy-cobalamin and about 250 mcg of methylcobalamin, about 50 mg of Vitamin C administered as about 56 mg of sodium ascorbate, about 5 mg of elemental magnesium administered as about 60 mg of magnesium 1-threonate, and a nutritionally acceptable carrier therefor.

Example 3

A nutritional supplement having a daily dose of:
about 0.4 mg of citrated folic acid (controlled release) and about 0.8 mg of levo-folinic acid moiety as the sodium salt of 6(S)-5-formyl-tetrahydrofolic acid,
about 30 mg of elemental iron administered in the form of about 272 mg of an iron amino acid chelate prepared according to the process of U.S. Pat. No. 7,341,708 using aspartic acid and cysteine,
about 200 mg of docosahexaenoic acid derived from fish oil having greater than 75% docosahexaenoic acid and less than 2% eicosapentaenoic acid,
about 25 mcg of Vitamin $B_1$ administered as thiamine pyrophosphate,
about 25 mcg of Vitamin $B_2$ administered as flavin adenine dinucleotide hydrate,
about 25 mcg of Vitamin $B_3$ administered as nicotinamide adenine dinucleotide,
about 1 mg of Vitamin $B_6$ administered as pyridoxal 5' phosphate,
about 500 mcg of Vitamin $B_{12}$ administered as about 250 mcg of 5'-deoxyadensosyl-cobalamin and about 250 mcg of methylcobalamin,
about 50 mg of Vitamin C administered as about 56 mg of sodium ascorbate,
about 5 mg of elemental magnesium administered as about 60 mg of magnesium 1-threonate, and
a nutritionally acceptable carrier therefor.

Example 4

A nutritional supplement having a daily dose of:
about 0.4 mg of citrated folic acid (controlled release) and about 0.8 mg of levo-folinic acid moiety as the sodium salt of 6(S)-5-formyl-tetrahydrofolic acid,
about 30 mg of elemental iron administered in the form of about 272 mg of an iron amino acid chelate prepared according to the process of U.S. Pat. No. 7,341,708 using aspartic acid and cysteine,
about 200 mg of docosahexaenoic acid derived from fish oil having greater than 75% docosahexaenoic acid and less than 2% eicosapentaenoic acid,
about 25 mcg of Vitamin $B_1$ administered as thiamine pyrophosphate,
about 25 mcg of Vitamin $B_2$ administered as flavin adenine dinucleotide hydrate,
about 25 mcg of Vitamin $B_3$ administered as nicotinamide adenine dinucleotide,
about 1 mg of Vitamin $B_6$ administered as pyridoxal 5' phosphate,
about 500 mcg of Vitamin $B_{12}$ administered as about 250 mcg of 5'-deoxyadensosyl-cobalamin and about 250 mcg of methylcobalamin,
about 50 mg of Vitamin C administered as about 56 mg of sodium ascorbate,
about 2 mg of elemental copper,
about 10 mg of elemental zinc, and
a nutritionally acceptable carrier therefor.

Example 5

A nutritional supplement having a daily dose of:
about 1 mg of the folic acid,
about 27 mg of elemental iron administered in the form of about 245 mg of an iron amino acid chelate prepared using aspartic acid and cysteine according to the process of U.S. Pat. No. 7,341,708, about 200 mg of docosahexaenoic acid derived from fish oil having greater than 75% docosahexaenoic acid and less than 1% eicosapentaenoic acid, about 25 mcg of Vitamin $B_1$ administered as thiamine pyrophosphate, about 25 mcg of Vitamin $B_2$ administered as flavin adenine dinucleotide hydrate, about 25 mcg of Vitamin $B_3$ administered as nicotinamide adenine dinucleotide, about 1 mg of Vitamin $B_6$ administered as pyridoxal 5' phosphate, about 500 mcg of Vitamin $B_{12}$ administered as about 250 mg of 5'-deoxyadensosyl-cobalamin and about 250 mcg of methylcobalamin, about 15 mg of Vitamin C administered as equal amounts of magnesium ascorbate and zinc ascorbate (the magnesium and zinc in this exemplary supplement being provided via the magnesium ascorbate and zinc ascorbate, respectively), and a nutritionally acceptable carrier therefor.

Example 6

A nutritional supplement having a daily dose of:
about 1 mg of folic acid,
about 30 mg of elemental iron administered in the form of about 272 mg of an iron amino acid chelate prepared according to the process of U.S. Pat. No. 7,341,708 using aspartic acid and cysteine,
about 200 mg of docosahexaenoic acid derived from fish oil having greater than 75% docosahexaenoic acid and less than 1.5% eicosapentaenoic acid,
about 25 mcg of Vitamin $B_1$ administered as thiamine pyrophosphate,
about 25 mcg of Vitamin $B_2$ administered as flavin adenine dinucleotide hydrate,
about 25 mcg of Vitamin $B_3$ administered as nicotinamide adenine dinucleotide, about 1 mg of Vitamin $B_6$ administered as pyridoxal 5' phosphate,
about 500 mcg of Vitamin $B_{12}$ administered as about 250 mcg of 5'-deoxyadensosy-cobalamin and about 250 mcg of methylcobalamin,
about 50 mg of Vitamin C administered as about 56 mg of sodium ascorbate,
about 5 mg of elemental magnesium administered as about 60 mg of magnesium 1-threonate, and
a nutritionally acceptable carrier therefor.

Example 7

A nutritional supplement having a daily dose of:
about 1 mg of folic acid,
about 30 mg of elemental iron administered in the form of about 272 mg of an iron amino acid chelate prepared according to the process of U.S. Pat. No. 7,341,708 using aspartic acid and cysteine,
about 200 mg of docosahexaenoic acid derived from fish oil having greater than 75% docosahexaenoic acid and less than 2% eicosapentaenoic acid,
about 125 mcg of Vitamin $B_1$ administered as thiamine pyrophosphate,
about 125 mcg of Vitamin $B_2$ administered as flavin adenine dinucleotide hydrate,
about 125 mcg of Vitamin $B_3$ administered as nicotinamide adenine dinucleotide,
about 1 mg of Vitamin $B_6$ administered as pyridoxal 5' phosphate,
about 500 mcg of Vitamin $B_{12}$ administered as about 250 mcg of 5'-deoxyadensosyl-cobalamin and about 250 mcg of methylcobalamin,
about 50 mg of Vitamin C administered as about 56 mg of sodium ascorbate,
about 5 mg of elemental magnesium administered as about 60 mg of magnesium 1-threonate, and
a nutritionally acceptable carrier therefor.

Example 8

A nutritional supplement having a daily dose of:
about 1 mg of folic acid,
about 30 mg of elemental iron administered in the form of about 272 mg of an iron amino acid chelate prepared according to the process of U.S. Pat. No. 7,341,708 using aspartic acid and cysteine,
about 200 mg of docosahexaenoic acid derived from fish oil having greater than 75% docosahexaenoic acid and less than 1.5% eicosapentaenoic acid,
about 625 mcg of Vitamin $B_1$ administered as thiamine pyrophosphate,
about 625 mcg of Vitamin $B_2$ administered as flavin adenine dinucleotide hydrate,
about 625 mcg of Vitamin $B_3$ administered as nicotinamide adenine dinucleotide,
about 1 mg of Vitamin $B_6$ administered as pyridoxal 5' phosphate,
about 500 mcg of Vitamin $B_{12}$ administered as about 250 mcg of 5'-deoxyadensosy-cobalamin and about 250 mcg of methylcobalamin,
about 50 mg of Vitamin C administered as about 56 mg of sodium ascorbate,
about 5 mg of elemental magnesium administered as about 60 mg of magnesium 1-threonate, and
a nutritionally acceptable carrier therefor.

Example 9

A nutritional supplement having a daily dose of:
about 1 mg of folic acid
about 20 mg of elemental iron administered in the form of about 181 mg of an iron amino acid chelate prepared according to the process of U.S. Pat. No. 7,341,708 using aspartic acid and cysteine,
about 200 mg of docosahexaenoic acid derived from fish oil having greater than 75% docosahexaenoic acid and less than 2% eicosapentaenoic acid,
about 25 mcg of Vitamin $B_1$ administered as thiamine pyrophosphate,
about 25 mcg of Vitamin $B_2$ administered as flavin adenine dinucleotide hydrate,
about 25 mcg of Vitamin $B_3$ administered as nicotinamide adenine dinucleotide,
about 1 mg of Vitamin $B_6$ administered as pyridoxal 5' phosphate,
about 500 mcg of Vitamin $B_{12}$ administered as about 250 mcg of 5'-deoxyadensosy-cobalamin and about 250 mcg of methylcobalamin,
about 50 mg of Vitamin C administered as about 56 mg of sodium ascorbate,
about 5 mg of elemental magnesium administered as about 60 mg of magnesium 1-threonate, and
a nutritionally acceptable carrier therefor.

15

Example 10

A nutritional supplement having a daily dose of:
about 1 mg of folic acid,
about 30 mg of elemental iron administered in the form of about 272 mg of an iron amino acid chelate prepared according to the process of U.S. Pat. No. 7,341,708 using aspartic acid and cysteine,
about 200 mg of docosahexaenoic acid derived from fish oil having greater than 75% docosahexaenoic acid and less than 2% eicosapentaenoic acid,
about 25 mcg of Vitamin $B_1$ administered as thiamine pyrophosphate,
about 25 mcg of Vitamin $B_2$ administered as flavin adenine dinucleotide hydrate,
about 25 mcg of Vitamin $B_3$ administered as nicotinamide adenine dinucleotide,
about 1 mg of Vitamin $B_6$ administered as pyridoxal 5' phosphate,
about 500 mcg of Vitamin $B_{12}$ administered as about 250 mcg of 5'-deoxyadensosyl-cobalamin and about 250 mcg of methylcobalamin,
about 50 mg of Vitamin C administered as about 56 mg of sodium ascorbate,
about 2 mg of elemental copper,
about 10 mg of elemental zinc, and
a nutritionally acceptable carrier therefor.

Example 11

A nutritional supplement having a daily dose of:
about 1 mg of folic acid,
about 30 mg of elemental iron administered in the form of about 272 mg of an iron amino acid chelate prepared according to the process of U.S. Pat. No. 7,341,708 using aspartic acid and cysteine,
about 200 mg of docosahexaenoic acid derived from fish oil having greater than 75% docosahexaenoic acid and less than 2% eicosapentaenoic acid,
about 625 mcg of Vitamin $B_1$ administered as thiamine pyrophosphate,
about 625 mcg of Vitamin $B_2$ administered as flavin adenine dinucleotide hydrate,
about 625 mcg of Vitamin $B_3$ administered as nicotinamide adenine dinucleotide,
about 1 mg of Vitamin $B_6$ administered as pyridoxal 5' phosphate,
about 500 mcg of Vitamin $B_{12}$ administered as about 250 mcg of 5'-deoxyadensosyl-cobalamin and about 250 mcg of methylcobalamin,
about 50 mg of Vitamin C administered as about 56 mg of sodium ascorbate,
about 2 mg of elemental copper,
about 10 mg of elemental zinc, and
a nutritionally acceptable carrier therefor.

Example 12

A nutritional supplement having a daily dose of:
about 1 mg of folic acid,
about 30 mg of elemental iron administered in the form of about 272 g of an iron amino acid chelate prepared according to the process of U.S. Pat. No. 7,341,708 using aspartic acid and cysteine,
about 200 mg of docosahexaenoic acid derived from fish oil having greater than 75% docosahexaenoic acid and less than 2% eicosapentaenoic acid,

16 about 625 mcg of Vitamin $B_1$ administered as thiamine pyrophosphate,
about 625 mcg of Vitamin $B_2$ administered as flavin adenine dinucleotide hydrate,
about 625 mcg of Vitamin $B_3$ administered as nicotinamide adenine dinucleotide,
about 1 mg of Vitamin $B_6$ administered as pyridoxal 5' phosphate,
about 500 mcg of Vitamin $B_{12}$ administered as about 250 mcg of 5'-deoxyadensosyl-cobalamin and about 250 mcg of methylcobalamin,
about 15 mg of Vitamin C administered as equal amounts of magnesium ascorbate and zinc ascorbate (the magnesium and zinc in this exemplary supplement being provided via the magnesium ascorbate and zinc ascorbate, respectively), and
a nutritionally acceptable carrier therefor.

Example 13

A nutritional supplement having a daily dose of:
an amount of a citrated folic acid material containing about 1 mg of folic acid,
about 30 mg of elemental iron administered in the form of about 272 mg of an iron amino acid chelate prepared according to the process of U.S. Pat. No. 7,341,708 using aspartic acid and cysteine,
about 200 mg of docosahexaenoic acid derived from fish oil having greater than 75% docosahexaenoic acid and less than 2% eicosapentaenoic acid,
about 625 mcg of Vitamin $B_1$ administered as thiamine pyrophosphate,
about 625 mcg of Vitamin $B_2$ administered as flavin adenine dinucleotide hydrate,
about 625 mcg of Vitamin $B_3$ administered as nicotinamide adenine dinucleotide,
about 1 mg of Vitamin $B_6$ administered as pyridoxal 5' phosphate,
about 500 mcg of Vitamin $B_{12}$ administered as about 250 mcg of 5'-deoxyadensosyl-cobalamin and about 250 mcg of methylcobalamin,
about 50 mg of Vitamin C administered as about 56 mg of sodium ascorbate,
about 2 mg of elemental copper,
about 10 mg of elemental zinc, and
a nutritionally acceptable carrier therefor.

Example 14

A nutritional supplement having a daily dose of:
an amount of a citrated folic acid material containing about 1 mg of folic acid,
about 30 mg of elemental iron administered in the form of about 272 g of an iron amino acid chelate prepared according to the process of U.S. Pat. No. 7,341,708 using aspartic acid and cysteine,
about 200 mg of docosahexaenoic acid derived from fish oil having greater than 75% docosahexaenoic acid and less than 2% eicosapentaenoic acid,
about 625 mcg of Vitamin $B_1$ administered as thiamine pyrophosphate,
about 625 mcg of Vitamin $B_2$ administered as flavin adenine dinucleotide hydrate,
about 625 mcg of Vitamin $B_3$ administered as nicotinamide adenine dinucleotide,
about 1 mg of Vitamin $B_6$ administered as pyridoxal 5' phosphate, about 500 mcg of Vitamin $B_{12}$ administered as about 250 mcg of 5'-deoxyadensosyl-cobalamin and about 250 mcg of methylcobalamin, about 15 mg of Vitamin C administered as equal amounts of magnesium ascorbate and zinc ascorbate (the magnesium and zinc in this exemplary supplement being provided via the magnesium ascorbate and zinc ascorbate, respectively), and a nutritionally acceptable carrier therefor.

Example 15

A nutritional supplement having a daily dose of:
an amount of a citrated folic acid material containing about 1 mg of folic acid, about 30 mg of elemental iron administered in the form of about 272 mg of an iron amino acid chelate prepared according to the process of U.S. Pat. No. 7,341,708 using aspartic acid and cysteine, about 200 mg of docosahexaenoic acid derived from fish oil having greater than 75% docosahexaenoic acid and less than 2% eicosapentaenoic acid, about 625 mcg of Vitamin $B_1$ administered as thiamine pyrophosphate, about 625 mcg of Vitamin $B_2$ administered as flavin adenine dinucleotide hydrate, about 625 mcg of Vitamin $B_3$ administered as nicotinamide adenine dinucleotide, about 1 mg of Vitamin $B_6$ administered as pyridoxal 5' phosphate, about 500 mcg of Vitamin $B_{12}$ administered as about 250 mcg of 5'-deoxyadensosyl-cobalamin and about 250 mcg of methylcobalamin, about 50 mg of Vitamin C administered as sodium ascorbate, about 2 mg of elemental copper, about 10 mg of elemental zinc, about 5 mg of elemental magnesium administered as magnesium l-threonate, and a nutritionally acceptable carrier therefor.

Example 16

A nutritional supplement having a daily dose of:
about 1 mg of folic acid, about 30 mg of elemental iron administered in the form of about 272 mg of an iron amino acid chelate prepared according to the process of U.S. Pat. No. 7,341,708 using aspartic acid and cysteine, about 200 mg of docosahexaenoic acid derived from fish oil having greater than 75% docosahexaenoic acid and less than 2% eicosapentaenoic acid, about 625 mcg of Vitamin $B_1$ administered as thiamine pyrophosphate, about 625 mcg of Vitamin $B_2$ administered as flavin adenine dinucleotide hydrate, about 625 mcg of Vitamin $B_3$ administered as nicotinamide adenine dinucleotide, about 1 mg of Vitamin $B_6$ administered as pyridoxal 5' phosphate, about 500 mcg of Vitamin $B_{12}$ administered as about 250 mcg of 5'-deoxyadensosyl-cobalamin and about 250 mcg of methylcobalamin, about 50 mg of Vitamin C administered as sodium ascorbate, about 2 mg of elemental copper, about 10 mg of elemental zinc, about 5 mg of elemental magnesium administered as magnesium l-threonate, and a nutritionally acceptable carrier therefor.

Examples 17-22

Examples 5-10 are repeated using an amount of a citrated folic acid material containing about 1 mg of folic acid in place of the about 1 mg of folic acid in each Example. For example, about 20 mg of a citrated folic acid material containing 5% folic acid (that is, about 1 mg of folic acid) is used in place of the about 1 mg of folic acid in each of Examples 5-10.

Exemplary nutritionally acceptable carriers are a combination of glycine, L-lysine acetate, L-glutathione, hesperidin complex, tripotassium citrate, citric acid, olive oil, sunflower lecithin and yellow beeswax in amounts suitable for formulating the supplements of the present invention as liquid-filled soft gelatin capsules; and a combination of caramel, citric acid, gelatin, glycerin, glycine, hesperidin complex, L-lysine acetate, L-glutathione, sunflower lecithin, natural orange (for flavor), olive oil, purified water, tripotassium citrate, and yellow beeswax in amounts suitable for formulating the supplements of the present invention as liquid-filled soft gelatin capsules. Other vegetable oils can be substituted for the olive oil in the above exemplary nutritionally acceptable carriers.

The embodiments of the present invention can be or are, as shown in the above Examples, free or substantially free of other added vitamins and minerals (as those words have been defined above). Additionally, the embodiments of the present invention can be or are, as shown in the above Examples, free or substantially free of pharmaceutically active agents (in this regard, the ingredients in the supplements of the present invention are considered nutritional agents and not pharmaceutically active agents).

The nutritional supplements of the present invention should be manufactured in accordance with the Current Good Manufacturing Practices in Manufacturing, Packaging, Labeling and Holding Operations for Dietary Supplements as promulgated by the Federal Food and Drug Administration, as the same may be amended from time to time, and other applicable regulations. It has been found that, when providing multiple vitamins in a dietary or nutritional supplement, some degradation of certain of the vitamins may occur over time. Accordingly, the manufacturing specifications for the vitamins should be about 100% to about 175%, preferably about 100% to about 160%, of the dosage amounts set forth above with respect to various embodiments of the present invention. The manufacturing specifications for the other ingredients should be about 100% to 135%, preferably about 100% to about 130%, of the dosage amounts set forth above with respect to various embodiments of the present invention.

While various embodiments of the present invention have been described, it should be understood that various modifications and adaptations thereof will be apparent to one skilled in this art. Such modifications and adaptations are considered to be within the scope of the present invention, which is limited only by the scope of the following claims.

What is claimed is:

1. A nutritional supplement consisting of twelve active ingredients and a nutritionally acceptable carrier therefor, wherein said active ingredients consist of a daily dose (all on a label claim basis) of the following twelve (and only twelve) active ingredients:

about 1 mg of folic acid or an amount of a citrate buffered folic acid material containing about 1 mg of folic acid,
about 30 mg of elemental iron administered in the form of an amino acid chelate prepared using aspartic acid and cysteine,
about 200 mg of docosahexaenoic acid,
about 625 mcg of Vitamin $B_1$ administered as thiamine pyrophosphate,
about 625 mcg of Vitamin $B_2$ administered as flavin adenine dinucleotide hydrate,
about 625 mcg of Vitamin $B_3$ administered as nicotinamide adenine dinucleotide,
about 1 mg of Vitamin $B_6$ administered as pyridoxal 5' phosphate,
about 500 mcg of Vitamin $B_{12}$ administered as about 250 mcg of 5'-deoxyadensosyl-cobalamin and about 250 mcg of methylcobalamin,
about 50 mg of Vitamin C administered as sodium ascorbate,
about 2 mg of elemental copper,
about 10 mg of elemental zinc, and
about 5 mg of elemental magnesium administered as magnesium 1-threonate,
wherein said supplement is suitable for supplementing the daily nutritional diet of a woman desiring to become pregnant, or a pregnant or nursing woman, and is free of other vitamins or minerals in nutritionally effective amounts.

2. The nutritional supplement of claim 1 wherein the supplement is in the form of one or more soft gelatin capsules.

3. The nutritional supplement of claim 1 wherein the supplement has about 1 mg of folic acid.

4. The nutritional supplement of claim 3 wherein the supplement is in the form of one or more soft gelatin capsules.

5. The nutritional supplement of claim 1 wherein the supplement has an amount of a citrate buffered folic acid material containing about 1 mg of folic acid.

6. The nutritional supplement of claim 5 wherein the supplement is in the form of one or more soft gelatin capsules.

7. The nutritional supplement of claim 1 wherein the copper is administered as a copper amino acid chelate and the zinc is administered as a zinc amino acid chelate.

8. The nutritional supplement of claim 7 wherein the supplement is in the form of one or more soft gelatin capsules.

9. A method of supplementing the daily nutritional diet of a woman desiring to become pregnant, or a pregnant or nursing woman comprising orally administering to such a woman the supplement of claim 3 on a daily basis.

10. A method of supplementing the daily nutritional diet of a woman desiring to become pregnant, or a pregnant or nursing woman comprising orally administering to such a woman the supplement of claim 5 on a daily basis.

11. A method of supplementing the daily nutritional diet of a woman desiring to become pregnant, or a pregnant or nursing woman comprising orally administering to such a woman the supplement of claim 7 on a daily basis.

* * * * *